(12) United States Patent
Ma et al.

(10) Patent No.: US 9,598,671 B2
(45) Date of Patent: Mar. 21, 2017

(54) **CYPRINID HERPESVIRUS II-SENSITIVE BRAIN TISSUE CELL LINE OF *CARASSIUS AURATUS GIBELIO* AND ESTABLISHING METHOD AND USE THEREOF**

(71) Applicant: Yangtze River Fisheries Research Institute, Chinese Academy of Fishery Science, Wuhan, Hubei (CN)

(72) Inventors: Jie Ma, Hubei (CN); Lingbing Zeng, Hubei (CN); Nan Jiang, Hubei (CN); Qian Chen, Hubei (CN); Hui Zhao, Hubei (CN)

(73) Assignee: YANGTZE RIVER FISHERIES RESEARCH INSTITUTE, CHINESE ACADEMY OF FISHERY SCIENCES, Wuhan, Hubei (CN)

( * ) Notice: Subject to any disclaimer, the term of this patent is extended or adjusted under 35 U.S.C. 154(b) by 0 days.

(21) Appl. No.: 14/774,041

(22) PCT Filed: Dec. 3, 2014

(86) PCT No.: PCT/CN2014/092954
§ 371 (c)(1),
(2) Date: Sep. 9, 2015

(87) PCT Pub. No.: WO2015/085886
PCT Pub. Date: Jun. 18, 2015

(65) Prior Publication Data
US 2016/0017284 A1    Jan. 21, 2016

(30) Foreign Application Priority Data
Dec. 9, 2013   (CN) .......................... 2013 1 0658939

(51) Int. Cl.
*C12N 5/079*    (2010.01)
*A61K 39/245*   (2006.01)
*C12Q 1/70*     (2006.01)
*G01N 33/50*    (2006.01)
*C12N 7/00*     (2006.01)

(52) U.S. Cl.
CPC .......... *C12N 5/0618* (2013.01); *A61K 39/245* (2013.01); *C12N 7/00* (2013.01); *C12Q 1/705* (2013.01); *G01N 33/5005* (2013.01); *C12N 2503/02* (2013.01); *C12N 2710/16034* (2013.01); *C12N 2710/16052* (2013.01)

(58) Field of Classification Search
None
See application file for complete search history.

(56) References Cited

FOREIGN PATENT DOCUMENTS

| CN | 102399743 | 4/2012 |
|---|---|---|
| CN | 103045764 | 4/2013 |
| CN | 103667176 | 3/2014 |

OTHER PUBLICATIONS

Wang et al., "Mass morality caused by Cyprinid Herpesvirus 2 (CyHV-w) in Prussian carp (Carassius gibelio) in China", Bulletin of the European Association of Fish Pathologists, Dec. 31, 2012, vol. 32(5), pp. 164-173.

Li et al., "Molecular surveillance of Cyprinid herpesvirus 2 in goldfish cultured in China", Journal of Huazhong Agricultural University, Jan. 31, 2013, vol. 32(1), pp. 92-96.

Xu et al., "Cyprinid herpesvirus 2 infection emerged in cultured gibel carp, Carassius auratus gibelio in China", Veterinary Microbiology, Sep. 27, 2013, vol. 166(1-2), pp. 138-144.

*Primary Examiner* — Karen Cochrane Carlson
*Assistant Examiner* — Jennifer M. H. Tichy
(74) *Attorney, Agent, or Firm* — Muncy, Geissler, Olds & Lowe, P.C.

(57) ABSTRACT

The present invention discloses a cyprinid herpesvirus II-sensitive brain tissue cell line of *Carassius auratus gibelio* and establishing method and use thereof. The cell line is deposited in China Center for Type Culture Collection under an accession number of CCTCC No: C2013179. The brain tissue cell line of *Carassius auratus gibelio* is in good growth state and sensitive to CyHV-2 that is presently hardly cultured with ordinary fish cell lines. After six passages of CyHV-2 in GiCB cells, viral nucleic acid can still be detected and a cytopathic effect is stable. When ultrathin microscopic sections are prepared from cells having the cytopathic effect, considerable mature CyHV-2 virions and their replication process can be observed in GiCB cells. The construction method of the brain tissue cell line of *Carassius auratus gibelio* of the present invention has high repeatability, scientific and reasonable conditions.

2 Claims, 3 Drawing Sheets

CYPRINID HERPESVIRUS II-SENSITIVE BRAIN TISSUE CELL LINE OF *CARASSIUS AURATUS GIBELIO* AND ESTABLISHING METHOD AND USE THEREOF

FIELD OF THE INVENTION

The invention belongs to the field of hydrobiological cell and the field of diseases prevention and control in aquiculture, and particularly relates to cyprinid herpesvirus II-sensitive brain tissue cell line of *Carassius auratus gibelio*, an establishing method of the cell line and uses of the cell line.

BACKGROUND OF THE INVENTION

Cyprinid herpesvirus II (CyHV-2), also known as Herpesviral haematopoietic necrosis virus (HVHN) or Goldfish haematopoietic necrosis virus (GFHNV) is classified as a member of the genus *Cyprinivirus*, the family Alloherpesviridae, together with the other two Herpesviruses of Cyprinid fish family, CyHV-1 (Carp pox) and CyHV-3 (Koi herpesvirus, KHV). CyHV-2 was first reported in 1995 to cause huge economic losses to goldfish culture in western Japan from 1992 to 1993 and the mortality for the infected goldfish was as high as 100%, followed by reports of a successive outbreaks of such disease in other countries and regions. In the spring of 1997, a large number of deaths occur in the US west coast for circulating aquaculture juvenile goldfishes, and the mortality was up to more than 80%, which was confirmed later by CyHV-2 infection. The international trade of ornamental fish is largely contributed to the global spread of the disease, and soon afterwards, the disease outbreaks successively in cultured goldfishes in Taiwan, Australia and the United Kingdom. In 2011, Hungary reported that CyHV-2 infection was also found in the cultured *Carassius auratus gibelio*. Since 2009, haematopoietic necrosis in crucian carp caused by CyHV-2 outbreaks in Jiangsu Province, China's major crucian carp culture areas. By mid-June 2012, an area of over 100,000 acres in the regions as Sheyang, Dafeng, Yandu, Baoying, Gaoyou, Xinghua, Hongze, Chuzhou in Jiangsu Province occurred disease, the mortality in the diseased ponds were up to 90%, and the economic losses has reached several hundred of millions. Meanwhile, in Hubei, Hunan, Jiangxi and Heilongjiang Provinces, CyHV-2 was also detected in the bodies of affected crucian carps. The virus has strong infectiousness and high mortality, causes huge economic losses to crucian carp and goldfish aquaculture, and seriously threatens to the development of crucian carp and goldfish aquaculture.

Cell culture and separation technique is the most accurate method in the diagnosis of virus disease, and it is usually recommended by the World Organization for Animal Health (OIE) as the preferred method for the detection of fish virus. However it has been found very difficult to proliferate CyHV-2 in common cell lines for the isolation of fish virus. Fathead minnow (FHM) cells, epithelioma popuasum cuprini (EPC) cells, eel kidney (EK-1) cells, chinook salmon embryo (CHSE-214) cells, rainbow trout gonad (RTG-2) cells and tilapia ovary (TO-2) cells are not sensitive to CyHV-2, only koi fin 1 (KF-1) cells can produce cytopathic effect (CPE). However, after three passages of the virus in KF-1 cells, CPE disappeared and no viral nucleic acid can be detected. Due to the lack of CyHV-2-sensitive cell lines, the study of CyHV-2 is limited, thus the establishment of a CyHV-2-sensitive cell line and study of its biological characteristics are of great significance to consecutive passage amplified culture of CyHV-2 and deep study of the characteristics of the virus. The present invention establishes a sensitive cell line GiCB for isolation and culture of cyprinid herpesvirus II. The application of the cell line includes but not limited to: development of physical and chemical properties, morphogenesis, virus infection approach, infection mechanism of cyprinid herpesvirus II and other fish viruses at molecular level; preparation, screen or evaluation of fish antiviral drugs.

SUMMARY OF THE INVENTION

An object of the present invention is to provide a cyprinid herpesvirus II-sensitive brain tissue cell line of *Carassius auratus gibelio*. The cell line can be used for isolation, detection and culture of cyprinid herpesvirus II. The cell line was deposited in China Center for Type Culture Collection (CCTCC) under a classification of Gibel carp, *Carassius auratus gibelio* (GiCB) with an accession number of CCTCC NO: C2013179 on Nov. 29, 2013. Address: Wuhan University, Wuhan, China.

It is confirmed that the deposit of accession number CCTCC NO: C2013179 in China Center for Type Culture Collection (CCTCC) has been made under the Budapest Treaty. Furthermore, the materials deposited under accession number CCTCC NO: C2013179 in China Center for Type Culture Collection (CCTCC) will be irrevocably and without restriction or condition be released to the public upon issuance of a patent.

Another object of the present invention is to provide a method for establishing the cyprinid herpesvirus II-sensitive brain tissue cell line of *Carassius auratus gibelio*. The method is simple and easy to operate.

The final object of the present invention is to provide uses of the cyprinid herpesvirus II-sensitive brain tissue cell line of *Carassius auratus gibelio*. The cell line can be used for isolation, detection and culture of cyprinid herpesvirus II; and for the continuous passage and amplified culture of CyHV-2 and thus for the future study of the characteristics of the virus.

To achieve the above objects, the present invention provides the following technical solutions:

A method for establishing a cyprinid herpesvirus II-sensitive brain tissue cell line of *Carassius auratus gibelio*, comprising the steps of:

(1) Treatment of the brain tissue: removing the brain tissue of *Carassius auratus gibelio* under sterile conditions, and subjecting to sterile treatment to obtain tissue blocks of 50-100 $mm^3$;

(2) Primary culture: digesting the tissue blocks of step 1) with trypsin solution special for tissue separation for 10-15 min, shaking 3-4 times, adding an equal volume of culture solution special for brain tissue cells of *Carassius auratus gibelio*, pipetting uniformly, centrifuging and collecting the digested cells, removing supernatant, adding culture solution, pipetting cell pellets, culturing the obtained cell suspension in a culture flask for cells, and changing half amount of the culture solution every two days;

(3) Subculture: having grown the primary cultured brain tissue of *Carassius auratus gibelio* into a monolayer, adding 0.25% W/V trypsin solution and standing for 2 min, suspending the cells in a culture solution, subculturing by inoculating the cells in a way of one flask into two flasks; subjecting the cells to next passage culture according to the above subculture method after forming a cell monolayer again, to obtain a cyprinid herpesvirus II-sensitive brain tissue cell line of *Carassius auratus gibelio*, GiCB; the cell line of which being deposited in China Center for Type Culture Collection (CCTCC) under a classification of Gibel carp, *Carassius auratus gibelio* (GiCB) with an accession number of CCTCC NO: C2013179 on Nov. 29, 2013; Address: Wuhan University, Wuhan, China.

The brain tissue cell line of *Carassius auratus gibelio* GiCB is fibroblast-like cell. The optimal medium is M199. The optimal volume fraction of serum is 20% (V/V). The optimal culture temperature is 25° C. After the GiCB cells are frozen in liquid nitrogen and then recovered and stained, about 80% of the cells have cell activity and keep original growth tendency. The cells have been steadily subcultured to passage 65.

Said trypsin solution special for tissue separation is 0.5%-0.7% W/V trypsin solution; the cell culture and subculture is performed at a temperature of 25-28° C., pH 7.0-7.4.

Said culture solution special for brain tissue cells of *Carassius auratus gibelio* is M199 culture medium containing 10-20% V/V fetal bovine serum, 10-20 ng/ml human basic fibroblast growth factor, 10-20 ng/ml human epidermal growth factor, 100 U/ml penicillin, 100 μg/ml streptomycin, 0.25 μg/ml amphotericin B, pH 7.0-7.4.

Uses of the cyprinid herpesvirus II-sensitive brain tissue cell line of *Carassius auratus gibelio*, including use of the cell line for culturing cyprinid herpesvirus II; use of the cell line for detecting cyprinid herpesvirus II; use of the cell line for isolating cyprinid herpesvirus II; use of the cell line for preparing cyprinid herpesvirus II vaccines; use of the cell line for isolating and detecting other fish viruses; use of the cell line as a biological model for screening anti-cyprinid herpesvirus II drugs; use of the cell line for gene transfection of fish cells and study of gene functions.

Said cyprinid herpesvirus II is a wide virulent strain of cyprinid herpesvirus II or a known separated strain of cyprinid herpesvirus II.

By detecting the DNA of cyprinid herpesvirus II consecutively subcultured in the GiCB cells using nested PCR detection method, as a result, it is demonstrated that the viral nucleic acid is still detectable after consecutive subcultured to passage 6 in GiCB cells; Cytopathic effect (CPE) is stable and obvious; the cells having cytopathic effect are observed by ultrathin section under electron microscope, the result of transmission electron microscope shows that CyHV-2 virions and their replication process are found in the cells, demonstrating that CyHV-2 has good biological activity in the GiCB cells.

With regard to the suspected CyHV-2 clinical diseased samples to be detected, on the basis that the nested PCR assay is positive, the suspected diseased samples are inoculated with the established GiCB cell line of the present invention, only 12 days later cytopathic effects such as cell vacuolation, cell fusion and cell monolayer detachment can be observed; after the suspected CyHV-2 clinical diseased samples to be detected are subcultured for more than 5 passages, the presence of the virus still can be detected by nested PCR.

The present invention has the following advantages as compared with the prior art:

(1) It has been found by research that CyHV-2 is very difficult to proliferate in common cell lines for the isolation of fish virus. Fathead minnow (FHM) cells, epithelioma popuasum cuprini (EPC) cells, eel kidney (EK-1) cells, chinook salmon embryo (CHSE-214) cells, rainbow trout gonad (RTG-2) cells and tilapia ovary (TO-2) cells are not sensitive to CyHV-2, only koi fin 1 (KF-1) cells can produce cytopathic effect (CPE). However after three passages of the virus in KF-1 cells, CPE disappeared and no viral nucleic acid can be detected. The present invention establishes a CyHV-2-sensitive brain tissue cell line of *Carassius auratus gibelio* by separating and culturing the CyHV-2-sensitive brain tissue cells of *Carassius auratus gibelio*.

(2) By detecting the DNA of cyprinid herpesvirus II consecutively subcultured in the GiCB cells, the present invention demonstrates that the viral nucleic acid is still detectable after consecutive subcultured to passage 6 in GiCB cells. Cytopathic effect (CPE) is stable and obvious; when an ultrathin electron microscopic section is prepared from cells having the cytopathic effect, the result of transmission electron microscope shows that CyHV-2 virions and their replication process are be observed in the cells, demonstrating that CyHV-2 has good biological activity in the GiCB cells.

Based on the isolation, detection and culture of cyprinid herpesvirus II, the present invention establishes a CyHV-2-sensitive cell line GiCB, provides a necessary technical platform for isolation, identification, and study of the complete biological characteristics of CyHV-2, and lays a foundation for the prevention and control of hematopoietic necrosis of crucian carp and goldfish.

DESCRIPTION OF DRAWINGS

in FIG. 1, A: primary brain tissue cells of *Carassius auratus gibelio*; B: the 32nd passage brain tissue cells of *Carassius auratus gibelio*.

in FIG. 3, A: normal GiCB cells as control; B: day 12 of the 1st passage GiCB cells infected with CyHV-2; C: day 12 of the 3rd passage GiCB cells infected with CyHV-2; D: day 12 of the 6th passage GiCB cells infected with CyHV-2.

DETAILED DESCRIPTION OF THE INVENTION

Figure 1:
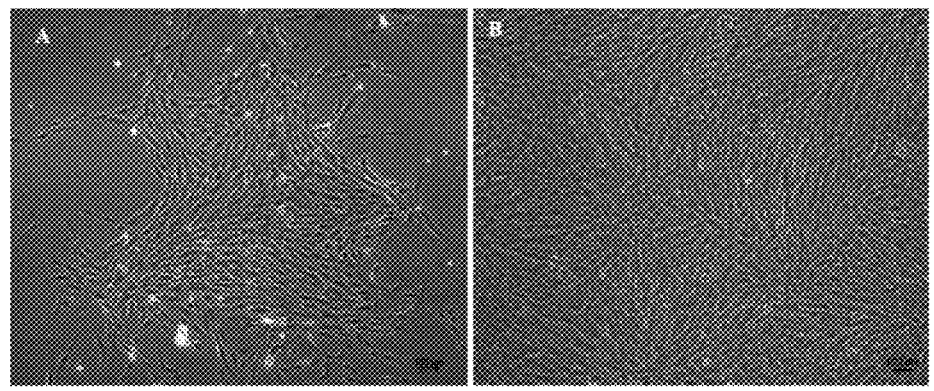
FIG. 1 is a schematic view of brain tissue cells of *Carassius auratus gibelio* GiCB at different passages.

The invention will be further described in detail below with reference to the particular examples. These examples are only illustrative and not intended to limit the present invention in any way. Various changes or modifications can be made without departing from the spirit and scope of the present invention, and these changes or modifications fall within the scope of the invention. Unless otherwise specified, the reagents used in the examples are purchased from biochemical reagent shops; and unless otherwise specified, the experimental techniques are conventional techniques.

Materials and reagents used in the particular examples of the invention:

1) Experimental Fish and Virulent Strain

*Carassius auratus gibelio*, about 50 g in weight, and about 12 cm in length, available from Yaowan experimental base of Yangtze Aquatic Research Institute, under Chinese Academy of Fishery Sciences, fed for one week before experiment. Cyprinid herpesvirus II, isolated and preserved by the our laboratory.

2) Main Reagents and Materials

M199 cell culture medium, Amphoterincin B, Penicillin/Streptomycin, Phosphoric acid buffer (PBS), trypsin-EDTA, Dimethyl Sulphoxide (DMSO), Colchicine, purchased from Sigma Company; Human basic fibroblast growth factor, Human epidermal growth factor, available from Peprotech Company; Fetal bovine serum, purchased from GIBICO Company; DNAzol nucleic acid extraction reagent, available from Invitrogen Company; rTaq enzyme, dNTPs for PCR, available from TaKaRa Company. Cell culture flasks, pipettes, freezing tubes, purchased from Corning Company; reagents and materials used for the preparation of Ultrathin section for transmission electron microscope, purchased from Beijing Zhongxingbairui Technology Co., Ltd.

3) Main Equipment and Instruments

Biological safety cabinet Class II (ESCO); Inverted microscope (Nikon); CCD camera (Nikon NIS Elements F530); Low-speed refrigerated centrifuge (3K15, Sigma); Thermostat incubator (Sanyo, MIR-153); Liquid nitrogen tank (MVE); Ultramicrotome (UC7, Leica); Transmission electron microscope (H-7650, Hitachi).

Example 1

Establishment of brain tissue cell line of *Carassius auratus gibelio*. The steps were as follows:

(1) Treatment of brain tissue: The brain tissue of *Carassius auratus gibelio* was removed under sterile conditions and placed in a culture dish, rinsed with PBS for 3 times, and cut into tissues blocks of 50-100 mm$^3$ with sterile ophthalmic scissors;

(2) Primary culture: the cut tissue blocks were placed in and digested with 0.5 W/V % trypsin solution at 28° C. for 15 min. Meantime, it was shaked for 3 times. After digestion, an equal volume of culture solution special for brain tissue cells of *Carassius auratus gibelio* (hereinafter called "culture solution" for short, the culture solution being M199 culture medium containing 20% V/V fetal bovine serum, 10 ng/ml human basic fibroblast growth factor, 10 ng/ml human epidermal growth factor, 100 U/ml penicillin, 100 µg/ml streptomycin, 0.25 µg/ml amphotericin B) was added and pipetted uniformly, followed by filtered once with 100 mesh nylon filter cloth. The filtrate was collected in a centrifuge tube, and centrifuged at 1500 rpm for 5 min to collect the cells treated by digestion and filtration. After removal of the supernatant, the cells were added with culture solution, pipetted uniformly, and filtered once with 300 mesh nylon filter cloth. The filtrate was collected and centrifuged at 1000 rpm for 5 min to collect the cell pellets; and then the culture solution was added to pipette the cell pellets. The obtained cell suspension was added in a 25 cm$^2$ cell flask and incubated at 25° C. Half amount of the solution was changed every two days.

(3) Subculture: After grew the primary cultured brain tissue of *Carassius auratus gibelio* into a monolayer, the original culture solution was removed and 2 ml 0.25 W/V % trypsin solution was added and placed still at room temperature for 2 min for digestion. The trypsin solution was removed and then 10 ml of culture solution special for brain tissue cells of *Carassius auratus gibelio* was added to spipette the cells at the bottom of the flask to obtain cell suspension, which was subcultured in a way by dividing the cells in one flask into two flasks. After a cell monolayer was formed again, the cells were subjected to next passage culture according to the above subculture method, until the cell line was established. After subcultured to passage 6, human basic fibroblast growth factor, human epidermal growth factor, penicillin, streptomycin and amphotericin B were no longer added to the culture solution special for brain tissue cells of *Carassius auratus gibelio*. The subcultured GiCB cells can cover about 80% of the bottom of the cell culture flask and formed confluent cell monolayer after about 2 or 3 days, and formed a dense cell monolayer after 5 days and then the next passage culture can be performed. As shown in FIG. 1, A represented primary brain tissue cells of *Carassius auratus gibelio*; B represented the 32$^{nd}$ passage brain tissue cells of *Carassius auratus gibelio*.

The cell line was deposited in China Center for Type Culture Collection (CCTCC) under a classification of GiCB (Gibel carp, *Carassius auratus gibelio*) with an accession number of CCTCC NO: 02013179 on Nov. 29, 2013; Address: Wuhan University, Wuhan, China.

Example 2

Biological characteristics of the brain tissue cell line of *Carassius auratus gibelio*, GiCB:

(1) Morphology: The cells are fibroblast-like cells.

(2) Growth properties: The passage GiCB cells began to adhere to the wall 30 min after subculture and completely adhered to the wall 8 h after subculture. The population doubling time was 50.5 h.

(3) Stability: The brain tissue cell line of *Carassius auratus gibelio*, GiCB, so far has been subcultured up to passage 65 and still grows in a stable proliferating status.

(4) Frozen storage and recovery:

After recovery, the GiGB cells adhered to the wall rapidly. The growth morphology, status was similar to the cells without frozen storage, and there was no significant difference. The recovered cells was stained with trypan blue and counted by cell statistics. About (80.38±5.10) % of the cells were not stained and had cell activities.

(5) Chromosome analysis

Figure 2:
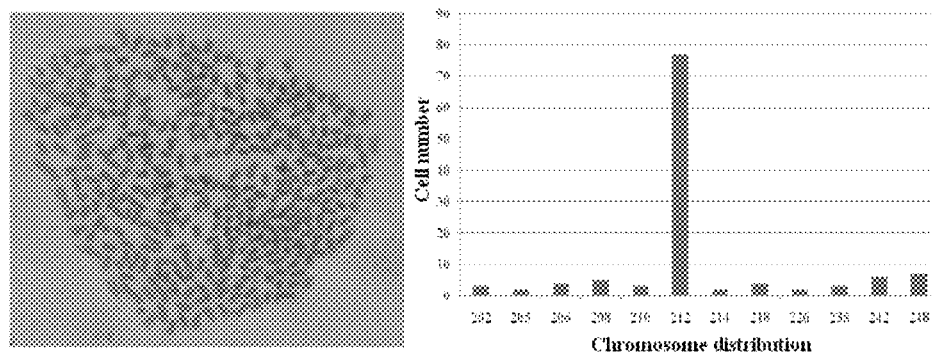
FIG. 2 is a schematic view of chromosomes and their number distribution of the 6th passage brain tissue cells of *Carassius auratus gibelio*.

The 6$^{th}$ passage brain tissue cell line of *Carassius auratus gibelio*, GiCB, was in the exponential growth phase. Colchicine was added with a final concentration of 20 µg/ml and incubated at 25° C. for 4 h and the cells were digested and collected, and treated with 0.075 mol/L KCl hypotonic solution for 25 min. Then pre-cooled carnoy's fluid was added and centrifuged at 1000 rpm for 5 min. After removal of the supernatant, it was fixed with carnoy's fluid for three times, 15 min each time. The sample was dropped on the slide by cold pendant drop method, after drying, it were stained with 5% Giemsa for 25 min, dried and then observed under a microscope. In the 100 observed cells at division phase, the 6$^{th}$ passage cells derived from the brain tissue of *Carassius auratus gibelio* had a chromosome number of 212 (FIG. 2), which was consistent with the characteristics of chromosomes of the artificial tetraploid *Carassius auratus gibelio* (Gui jianfang et al., *Discovery of Multiple Tetraploids in Artificially Propagated Populations of Carassius Auratus Gibelio and Their Breeding Potentialities*, Chinese Science Bulletin, 1992, 07:646-648; Gui jianfang et al., Preliminary Confirmation of Gynogenetic Reproductive Mode in Artificial Multiple Tetraploid Carassius auratus gibelio, Chinese Science Bulletin, 1992, 09: 836-838), namely including total 162 chromosomes of *Carassius auratus gibelio* and one genome of cyprinus carpio (50 chromosomes).

Example 3

The applications of the cyprinid herpesvirus II-sensitive cell line of *Carassius auratus gibelio*. The process was as follows:

(1) Collection and treatment of diseased sample infected with cyprinid herpesvirus II kidney and spleen were collected from the diseased fish infected with cyprinid herpesvirus II that had just died, cut into pieces and homogenized with equal volume of PBS, centrifuged at 6000 rpm at 4° C. for 30 min, filtered through 0.22 μm membrane filter to obtain sterile tissue homogenate, packed and stored at −80° C. for use.

(2) Proliferation of cyprinid herpesvirus II in GiCB

After GiCB was cultured to 80% monolayer cells, the medium was removed and the cells were washed twice with PBS. 1 ml of the above treated diseased tissue homogenate supernatant was inoculated into the cell monolayer. Polybrene was added with a final concentration of 10 μg/μl and incubated at 25° C. for 2 h, during which the flask was slightly shaken every 15-20 min so as to attach uniformly. After the attachment, it was incubated with M199 maintenance medium replacement containing 2% serum at 25° C. Cytopathic effect (CPE) was observed day by day, and viruses were harvested when cytopathic effect reached 80%.

(3) Extraction and nested PCR detection of cytotoxic nucleic acid of cyprinid herpesvirus II The significant cytopathic GiCB cells were frozen and thawed twice and then virus DNA was extracted with DNAzol reagent. The virus was detected according to the detection method for CyHV-2 by nested PCR.

PCR amplification conditions of outer primer P1: Primers:

```
CyHV-2P1F:                        (SEQ ID NO: 1)
TGAAATGTCAAAAGTGGATGG;

CyHV-2P1R:                        (SEQ ID NO: 2)
TATTCCCAGACAGCCTTCAAA.
```

Amplification conditions: pre-degeneration at 94° C. for 5 min, degeneration at 94° C. for 30 min, annealing at 55° C. for 30 min, extension at 72° C. for 40 s, 30 cycles; and 72° C. for 5 min;

PCR amplification conditions of inner primer P2: Primers:

```
CyHV-2P2F:                        (SEQ ID NO: 3)
GAACACCGCTGCTCATCATC;

CyHV-2P2R:                        (SEQ ID NO: 4)
ACTCTTCGCAAGTCCTCACC,
```

PCR amplification was performed using 1 μL of the amplified product of outer primer P1 as a template and inner primer P2 as a primer. The reaction conditions were the same as the first amplification. Meanwhile, positive control DNA template was used as a positive control and purified water was used as a negative control. The amplification product was identified by 2% (W/V) agarose gel electrophoresis.

(4) Observation of cyprinid herpesvirus II-infected GiCB by electron microscope

GiCB cells infected with the $5^{th}$ passage CyHV-2 cytotoxicity were fixed in 2% glutaraldehyde, postfixed in osmium tetroxide, dehydrated, embedded, cut into ultrathin sections, and stained with urangl acetate followed by lead citrate, then observed with transmission electron microscope.

(5) Results

Figure 3:
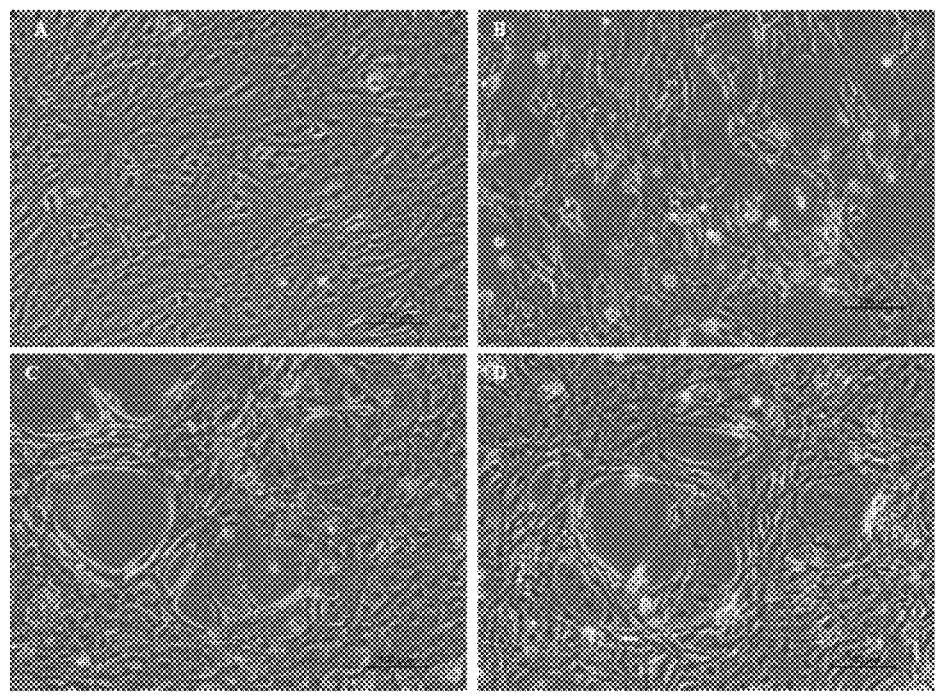
FIG. 3 is a schematic view of brain tissue cells of *Curassius auratus gibelio* infected with CyHV-2.

After 10 days of inoculation of the GiCB cell monolayer with cyprinid herpesvirus II-infected diseased tissue homogenate, the cells became round or vacuolated, retracted, formed syncytium, and the cell gaps became large; 12 days later, GiCB cells fused and formed multinucleated giant cells, and cell monolayer were detached and produced threads, which were typical cytopathic effects (CPE); and CPE was stable after subcultured to passage 6 (FIG. 3). However, no change was seen in normal cells.

Figure 4:
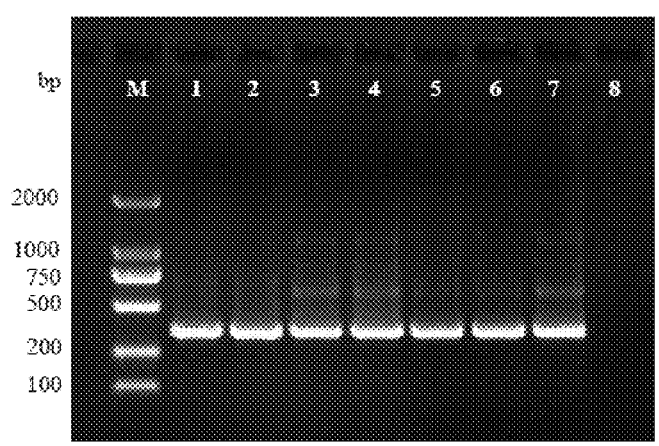
FIG. 4 is a schematic view of nested PCR detection results of CyHV-2 from different culture passages. M: DL2000 Marker; Line 1: CyHV-2 histotoxicity control; Line 2: the $1^{st}$ passage CyHV-2 cytotoxicity cultured in GiCB cells; Line 3: the $2^{nd}$ passage CyHV-2 cytotoxicity cultured in GiCB cells; Line 4: the $3^{rd}$ passage CyHV-2 cytotoxicity cultured in GiCB cells; Line 5: the $4^{th}$ passage CyHV-2 cytotoxicity cultured in GiCB cells; Line 6: the $5^{th}$ passage CyHV-2 cytotoxicity cultured in GiCB cells; Line 7: the $7^{th}$ passage CyHV-2 cytotoxicity cultured in GiCB cells; Line 8: negative control.

DNA was extracted from different passages of CyHV-2 cell culture, and amplified by two cycles of PCR amplification to obtain a 357 bp fragment, which was identical to the amplified band of the positive control (FIG. 4). The results were all determined as positive.

Figure 5:
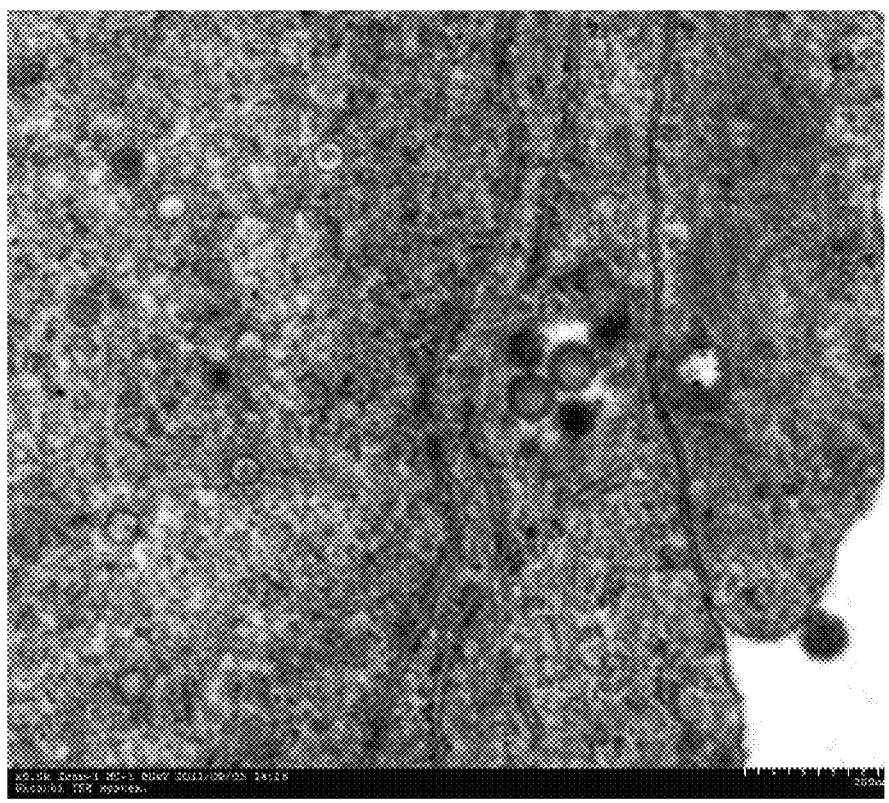
FIG. 5 is a schematic view of electron microscope ultrathin sections of GiCB cells infected with the $5^{th}$ passage CyHV-2 cytotoxicity.

By observing the GiCB cells infected with the 5th passage CyHV-2 cytotoxicity through transmission electron microscope, a large number of mature CyHV-2 virions and their replication process can be observed, demonstrating that CyHV-2 had good biological activity in GiCB cells (FIG. 5), which further demonstrated that the brain tissue cell line of *Carassius auratus gibelio* established by the present invention was sensitive to the virus, and can be used for the isolation, culture and detection of the virus. Meanwhile, it can be used as a cell model for study of the biological characteristics of cyprinid herpesvirus II, preparation of cyprinid herpesvirus II vaccine and screening of antiviral drugs.

---

What is claimed is:

1. A method for culturing cyprinid herpesvirus II, comprising:
   providing a tissue homogenate from diseased *Carassius auratus gibelio* infected with cyprinid herpesvirus II,
   culturing a cyprinid herpesvirus II-sensitive brain tissue cell line, named GiCB, derived from a brain tissue of *Carassius auratus gibelio*, deposited in China Center for Type Culture Collection (CCTCC) under accession number CCTCC NO: C2013179, to 80% monolayer cells, and
   inoculating a supernatant of the tissue homogenate into the cell monolayer.

2. A method for establishing a cyprinid herpesvirus II-sensitive brain tissue cell line, named GiCB, derived from a brain tissue of *Carassius auratus gibelio*, deposited in China Center for Type Culture Collection (CCTCC) under accession number CCTCC NO: C2013179, comprising the steps of:
   (1) treatment of brain tissue: removing brain tissue of *Carassius auratus gibelio* under sterile conditions, and subjecting the brain tissue to sterile treatment to obtain tissue blocks of 50-100 mm³;
   (2) primary culture: digesting the tissue blocks of step (1) above with a trypsin solution formulated for tissue separation for 10-15 min, shaking the combined tissue blocks and trypsin solution for 3 to 4 times, adding an equal volume of a culture solution formulated for brain tissue cells of *Carassius auratus gibelio*, pipetting a resulting mixture uniformly, centrifuging and collecting resulting digested cells, removing supernatant, adding culture solution, pipetting resulting cell pellets, culturing an obtained cell suspension in a culture flask, and changing half an amount of the culture solution present every two days;
   (3) subculture: after the primary cultured brain tissue of *Carassius auratus gibelio* has grown into a monolayer, adding 0.25% W/V trypsin solution and standing a resulting mixture for 2 min, suspending the cells in a culture solution, subculturing the cells by inoculating the cells first in one flask, then dividing the cells into two flasks; after the cells form a cell monolayer again, subjecting the cells to a next passage culture according to the above subculture of the preceding portion of step (3), to obtain the cyprinid herpesvirus II-sensitive brain tissue cell line of *Carassius auratus gibelio*, GiCB;
   wherein said trypsin solution formulated for tissue isolation is a 0.5%-0.7% W/V trypsin solution;
   wherein cell culture and subculture is performed at a temperature of 25-28° C., and at a pH of 7.0-7.4; and
   wherein said culture solution formulated for brain tissue cells of *Carassius auratus gibelio* is an M199 culture medium containing 10-20% V/V fetal bovine serum, 10-20 ng/ml human basic fibroblast growth factor, 10-20 ng/ml human epidermal growth factor, 100 U/ml penicillin, 100 µg/ml streptomycin, 0.25 µg/ml amphotericin B, pH 7.0-7.4.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial sequence
<220> FEATURE:
<223> OTHER INFORMATION: CyHV-2P1 Forward primer

<400> SEQUENCE: 1
tgaaatgtca aaagtggatg g                                            21
```

-continued

```
<210> SEQ ID NO 2
<211> LENGTH: 21
<212> TYPE: DNA
<213> ORGANISM: Artificial sequence
<220> FEATURE:
<223> OTHER INFORMATION: CyHV-2P1 Reverse primer

<400> SEQUENCE: 2
tattcccaga cagccttcaa a                                              21

<210> SEQ ID NO 3
<211> LENGTH: 20
<212> TYPE: DNA
<213> ORGANISM: Artificial sequence
<220> FEATURE:
<223> OTHER INFORMATION: CyHV-2P2 Forward primer

<400> SEQUENCE: 3
gaacaccgct gctcatcatc                                                20

<210> SEQ ID NO 4
<211> LENGTH: 20
<212> TYPE: DNA
<213> ORGANISM: Artificial sequence
<220> FEATURE:
<223> OTHER INFORMATION: CyHV-2P2 Reverse primer

<400> SEQUENCE: 4
actcttcgca agtcctcacc                                                20
```